United States Patent
McGuire et al.

(10) Patent No.: US 7,541,547 B2
(45) Date of Patent: Jun. 2, 2009

(54) SYSTEM AND METHOD FOR MEASURING AND DISTRIBUTING MONETARY INCENTIVES FOR WEIGHT LOSS

(75) Inventors: Todd J. McGuire, Denver, CO (US); Jack D. Rule, Littleton, CO (US)

(73) Assignee: Incentahealth, LLC, Denver, CO (US)

(*) Notice: Subject to any disclaimer, the term of this patent is extended or adjusted under 35 U.S.C. 154(b) by 971 days.

(21) Appl. No.: 10/738,843

(22) Filed: Dec. 17, 2003

(65) Prior Publication Data

US 2004/0131997 A1 Jul. 8, 2004

Related U.S. Application Data

(60) Provisional application No. 60/435,126, filed on Dec. 19, 2002.

(51) Int. Cl.
*G01G 19/40* (2006.01)

(52) U.S. Cl. .......... 177/25.13; 177/25.16; 177/25.19; 177/245; 128/921; 340/5.82

(58) Field of Classification Search .......... 340/5.82; 177/25.11–25.17, 25.19, 245; 128/921
See application file for complete search history.

(56) References Cited

U.S. PATENT DOCUMENTS

| | | | | |
|---|---|---|---|---|
| 3,639,905 A | * | 2/1972 | Yaida et al. | 340/5.82 |
| 4,336,855 A | * | 6/1982 | Chen | 177/245 |
| 4,844,187 A | * | 7/1989 | Jabero | 177/5 |
| 5,415,176 A | * | 5/1995 | Sato et al. | 600/547 |
| 5,673,691 A | * | 10/1997 | Abrams et al. | 600/300 |
| 5,763,837 A | * | 6/1998 | Davignon et al. | 174/113 R |
| 6,038,465 A | * | 3/2000 | Melton, Jr. | 600/407 |
| 6,290,646 B1 | * | 9/2001 | Cosentino et al. | 600/300 |
| 6,336,136 B1 | * | 1/2002 | Harris | 709/219 |
| 6,402,691 B1 | * | 6/2002 | Peddicord et al. | 600/300 |
| 6,403,897 B1 | * | 6/2002 | Bluth et al. | 177/144 |
| 6,609,068 B2 | * | 8/2003 | Cranley et al. | 702/24 |
| 6,649,848 B2 | * | 11/2003 | Kriger | 177/25.13 |
| 6,811,516 B1 | * | 11/2004 | Dugan | 482/8 |

(Continued)

OTHER PUBLICATIONS www.realize-health.com; Aug. 4, 2004; Method to promote employee health by monitoring health goals and providing incentives to the employee.

(Continued)

*Primary Examiner*—Randy W Gibson
(74) *Attorney, Agent, or Firm*—Brownstein Hyatt Farber Schreck, LLP (57) ABSTRACT

An automated identification, weight measurement and data reporting system that allows users to have their weight measured at a remote location and sent electronically to a data center. The invention can use biometric identification technology to confirm the identity of the user at the time of the measurement of the user's weight. The user's body weight may be measured via an electronic scale connected to the biometric identification device. The measurement data is then sent via a network (such as the Internet) to a central database. This secure weight measurement data is then used to offer incentives to individuals to lose weight. The more weight an individual loses, the larger the earned incentives. The invention also includes programs to measure health functions and to provide incentives to improve their health including body fat reduction, quitting smoking, reducing their blood pressure, or other health function.

39 Claims, 4 Drawing Sheets

U.S. PATENT DOCUMENTS

| | | | |
|---|---|---|---|
| 6,852,069 B2* | 2/2005 | Park | 482/8 |
| 7,009,119 B2* | 3/2006 | Carlucci et al. | 177/199 |
| 7,163,516 B1* | 1/2007 | Pagnacco et al. | 600/595 |
| 7,170,016 B2* | 1/2007 | Dumornay et al. | 177/25.13 |
| 7,239,725 B2* | 7/2007 | Dobashi | 382/118 |
| 2002/0055857 A1* | 5/2002 | Mault | 705/2 |
| 2002/0089413 A1* | 7/2002 | Heger et al. | 340/5.82 |
| 2002/0139588 A1* | 10/2002 | Brandt | 177/25.16 |
| 2002/0173991 A1* | 11/2002 | Avitall | 705/2 |
| 2003/0093697 A1* | 5/2003 | Lin | 713/202 |
| 2003/0156011 A1* | 8/2003 | Modl et al. | 340/5.82 |
| 2003/0223905 A1* | 12/2003 | Moerman | 422/56 |
| 2003/0229512 A1* | 12/2003 | Lenhard, II | 705/2 |
| 2005/0075908 A1* | 4/2005 | Stevens | 705/2 |
| 2005/0101875 A1* | 5/2005 | Semler et al. | 600/509 |
| 2006/0294108 A1* | 12/2006 | Adelson et al. | 707/10 |

OTHER PUBLICATIONS

Realize Press Release; "Realize introduces New Corporate Weight-Loss and Management Solution"; Aug. 2, 2004; Business Wire (http://home.businesswire.com).

* cited by examiner

SYSTEM AND METHOD FOR MEASURING AND DISTRIBUTING MONETARY INCENTIVES FOR WEIGHT LOSS

CROSS REFERENCES TO RELATED APPLICATIONS

This application claims priority from an earlier U.S. Provisional Application Serial No. 60/435,126 filed in the United States Patent and Trademark Office on Dec. 19, 2002, the entire disclosure of which is incorporated by reference herein.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates to systems and methods of measuring and communicating an individual's health, and more particularly to electronic weight measurement devices. The invention also relates to methods for providing incentives based on a measured amount of weight loss.

2. Description of the Related Art

Today, 65% of adult Americans are overweight. Over 30% are obese. Healthcare costs are spiraling upward out of control. A major contributor to these escalating costs relates to our population being overweight. There is neither a lack of diet programs nor a lack of desire on the part of people to lose weight as evidenced by the weight loss industry having gross sales of $33B in 2001.

Current health care programs use an age-based pricing approach. If two individuals are 42 year old males with the same height, they pay the same premium, even if one individual has an ideal weight of 175 pounds (assuming a height of 5 feet 10 inches) and the other weighs 250 pounds. Currently, there is no external incentive to maintain a healthy weight.

Further, healthcare costs are affected dramatically by an individual's fitness and a significant impact could be made on the cost of healthcare if the American public could lose and maintain an acceptable lower body weight. Insurance carriers would experience lower claims, and consequently, the public would receive lower premiums.

Certainly, the $33B expenditure provides indisputable evidence that the American public has a sincere interest in taking off the extra pounds. It should come as no surprise that these diet programs and weight loss regimes are performing very poorly. In general, all of the diets have proven to be a dismal failure. They can be effective in the short term. Usually, after the initial period of weight loss, the dieter returns to the eating habits that were the cause of the overweight condition in the first place. As a result, 95% of dieters return to their pre-diet weight, or greater, within 5 years.

Though many programs have lowered individuals' weight levels for short periods of time, no solution has successfully helped individuals maintain the reduced weight levels over the long term. It is therefore desirable to provide an incentive program to maintain individual weight maintenance over the long term and to provide a weight loss incentive concept that is realistic, affordable, effective, and sustainable.

BRIEF SUMMARY OF THE INVENTION

In contrast to the current age-based approach to health care, a new approach to the overweight problem is to provide an ongoing incentive to the employees (and their families) of corporations, the government, and any other organization. Using targets based on industry guidelines such at the Body Mass Indicator (BMI), weight loss goals can be set for all overweight participants. Using a periodic measurement process (quarterly, monthly, etc.) the participant's weight can be measured. If the participant reduces his or her weight into a lower weight category, he or she may receive a monetary reward each month. As long as the participant keeps their weight down, they may continue to receive reward checks each month. To assist the participants in achieving their weight loss goals, the program can also provide support and information on diet and exercise.

Figure 3:
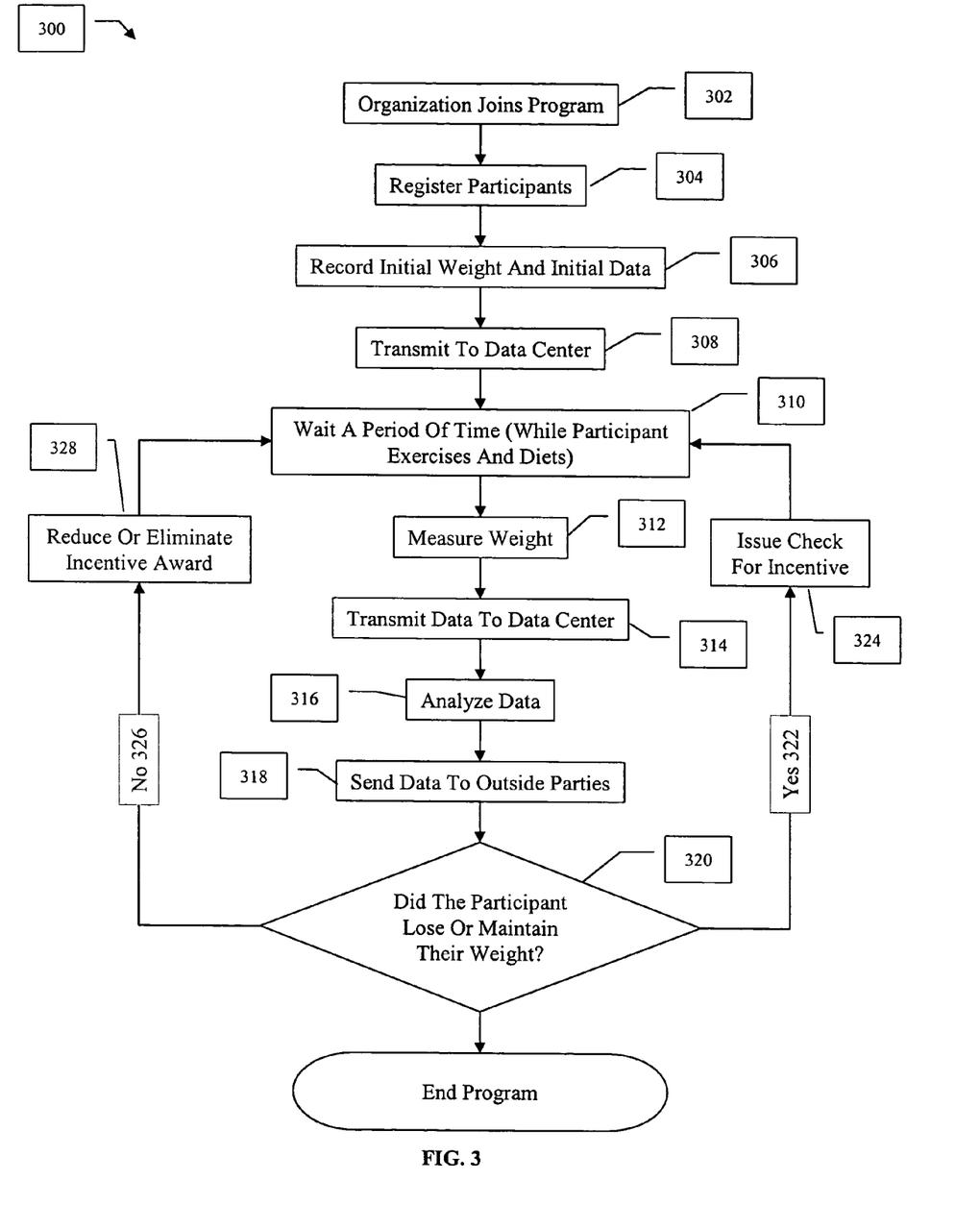
FIG. 3 shows one embodiment of a method to provide incentives to a participant in accordance with the present invention.

To clarify, each drawing includes reference numerals. These reference numerals follow a common nomenclature. The reference numeral will have three digits. The first digit represents the drawing number where the reference numeral was first used. For example, a reference numeral used first in drawing one will have a numeral like 1XX, while a numeral first used in drawing two will have a numeral like 2XX. The second two numbers represent a specific item within a drawing. One item in FIG. 1 may be 101 while another item may be 102. Like reference numerals used in later drawing represent the same item. For example, reference numeral 102 in FIG. 3 is the same item as shown in FIG. 1.

DETAILED DESCRIPTION OF THE INVENTION

Weight Loss Incentive System

Figure 1:
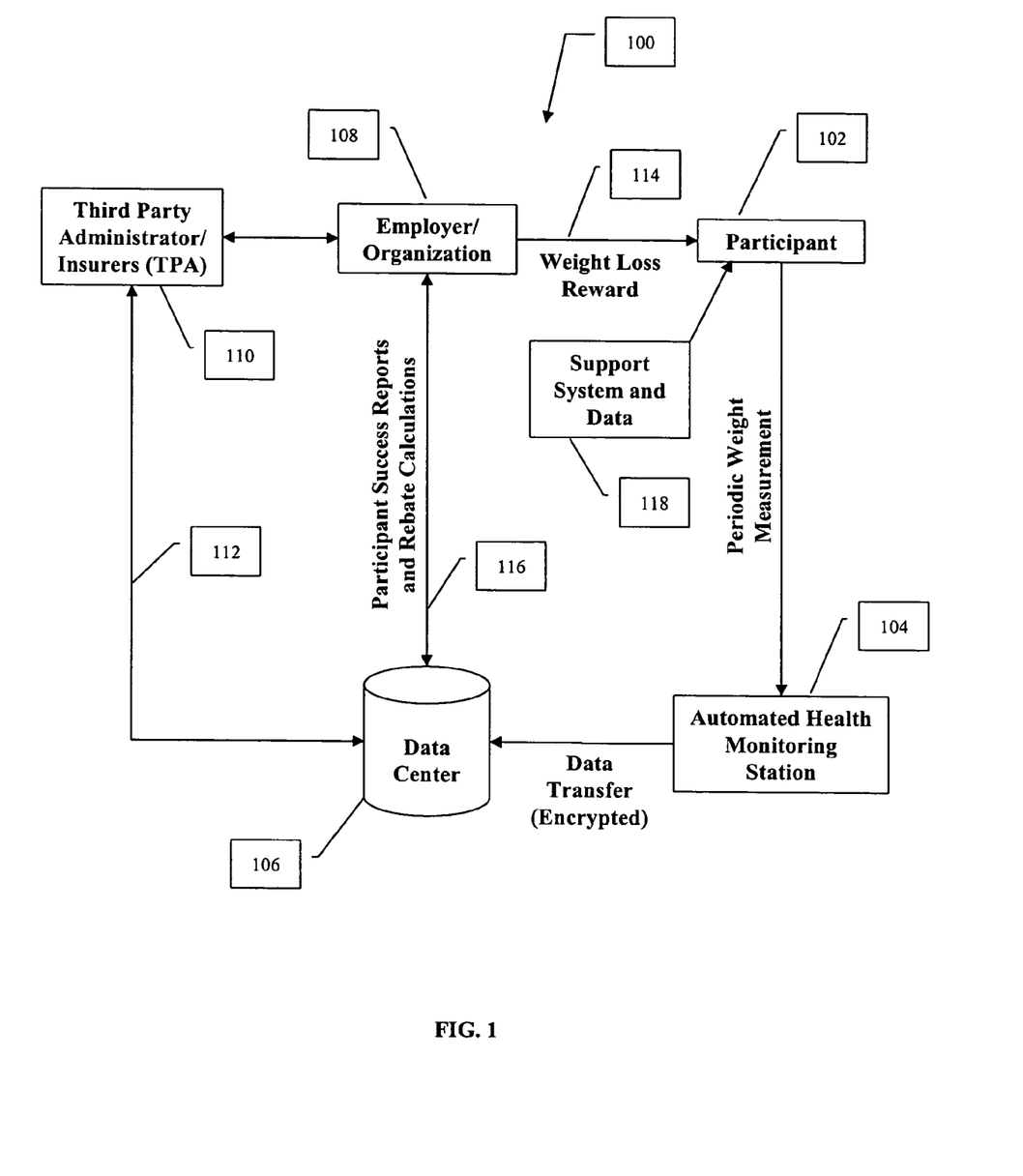
FIG. 1 shows one embodiment of a system for providing incentives to a participant in accordance with the present invention.

FIG. 1 shows an embodiment of a system to provide incentives to a participant 102 of a weight loss program or a weight management program. The system may include one or more of the following: one or more participants, one or more automated health monitoring stations 104, a data center 106, one or more employers 108, or one or more third party organizations or third party administrators 110. While these elements of the system are described in more detail below, the present invention is not limited to this one embodiment. Rather, one skilled in the art will recognize more, fewer, or different elements that may comprise the system.

The participant 102 is any person, or member of the participant's family or household that participates in the weight loss program or weight management program. This weight management or weight loss program is a service that the person 102 may enroll in that helps that person 102 lose or maintain a certain weight. A participant 102 may be involved by subscribing to the program through an employer 108 or organization 110. All of the components of the invention are targeted at helping these participants 102 lower their weight and maintain it at the target weight level. In some embodiments, the participant 102 may volunteer for the program. A participant 102 may also be recommended to the program by a doctor to improve the health of the participant 102.

An automated health monitoring station 104 may be any device that participants 102 use to measure some type of health data and submit the results for the weight loss program. This device 104 may include any type of weighing device 204, which may be automated or not automated. In an exemplary embodiment, the weighing device 204 is a digital scale that can output its reading to an external electronic device or system. The data collected by the station 104 can be securely stored to protect the participant's privacy during measurement. In other embodiments, the data may be transmitted to a computer 210 or over a network 212. An exemplary embodiment of an automated health monitoring station 104 is described further below.

Communicatively coupled to the automated health monitoring station 104 may be a data center 106. The data center 106 is the central repository of all data collected from the participants. The data center 106 may be any computer 210 or electronic database that can store data. Databases and the software and electronics that form databases are well known in the art and will not be explained further. In addition, the data center 106 represents the organization or entity that can assist either the employer 108 or third party organization 110 in providing the weight management program and assist in providing the monetary incentives 114. All participant data is securely stored to ensure participant privacy while the data resides in the data center 106. The data in the data center 106 can be used to calculate participant success, and the resulting monetary incentives 114 due to each participant 102. The monetary incentive 114 is any cash, credit to an account, or check provided or given to a participant 102 for losing weight or maintaining a healthy weight. An example of a credit to an account would be an electronic transfer to the participant's bank account.

The data center 106 may export or transmit the data to outside organizations or entities. One of these outside entities may be a third party administrator 110. Third party administrators 110 may include, but are not limited to, health insurance administers, health insurance companies, doctors, health maintenance organizations, hospitals, gyms, or diet companies. These third party administrators 110 may operate the program or simply use the weight loss data for other purposes. In another embodiment, a third party administrator 110 may include a health insurance company administrator. The health insurance company administrator can be an individual at the insurance company that oversees a given employer's participation in the incentive program. This individual or entity can view all of the detailed statistics on each participant's performance through an insurance company gateway 112. The insurance company gateway 112 is an application through which the health insurance company administrator can securely access the performance history of all participating participants 102 stored at the data center 106. The data center 106 can create the reports used to generate the reward checks for the appropriate participants 102.

Another outside entity may be the employer 108. The employers 108 write the checks to participants 102 (participants and their families) who successfully reduce their weight. However, in other embodiments, the data center 106 or third party administrator 110 may also write the checks to the employee 102. In any of these embodiments, the employer 108 or third party administrator 110 may reimburse the costs to the paying entity. Employers 108 can be any organization that has a relationship with the participant 102. Thus, the employer 108 may be a non-profit organization or charity, a company that hire's the participant 102, or some other organization. For instance, a health food store, such as General Nutrition Center (GNC) may house the health monitoring station. Customers of GNC or other people may use the station to weigh-in if that person does not have a relationship with an employer or does not have access to another station. Also, people may enroll in the weight loss program through GNC and use the station for their periodic weigh-ins. The customers may receive support from GNC, in the form of contest prizes and discounts at GNC, for successfully weighing in each month at a local GNC. In other embodiments, the health monitoring station may be located at and used in programs sponsored by WalMart, or Walgreens, or health clubs (like 24 Hour Fitness). One skilled in the art will recognize other organizations that may act in the role of the employer or organizational sponsor of the program. These other entities are included in the invention. The employer 108 may or may not have a monetary incentive 114 to lower the weight of its employees 102. In one embodiment, the employer 108 may be an employer health plan administrator. The employer health plan administrator is the main contact at the employer 108 that is in charge of administering the participant health insurance plan. This individual can access the health data covering the general success of the participants 102 in the program. This individual may also serve as the central receiving point for the quarterly reward checks. To access the data securely, the employer health plan administrator may access an employer health plan administrator gateway 116. This gateway application 116 lets the administrator view the data about the performance of the company's participants 102, in the data center 106, who are participating in the invention.

Automated Health Monitoring Station

Figure 2A:
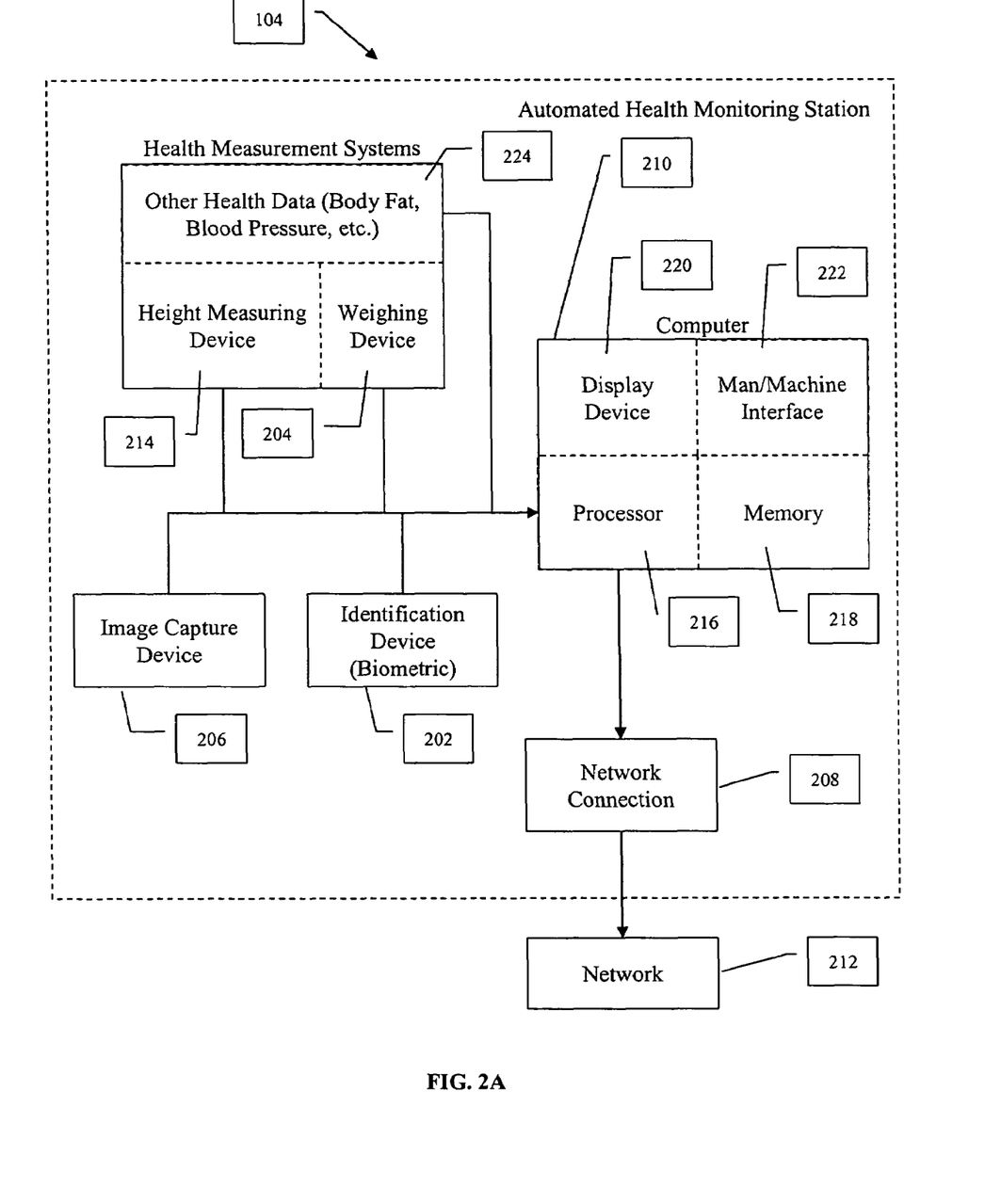
FIG. 2A shows one embodiment of an automated health monitoring station in accordance with the present invention.
Figure 2B:
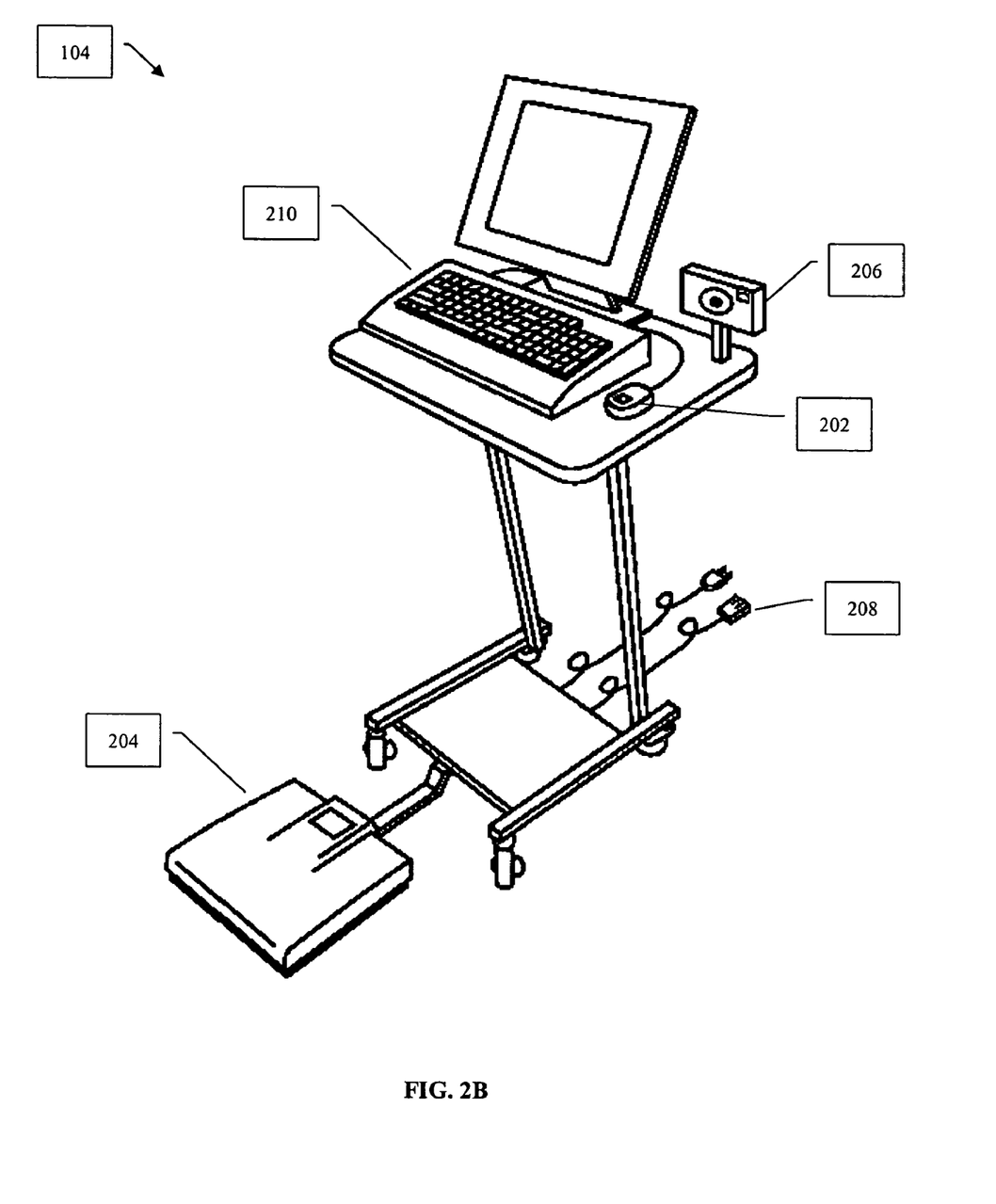
FIG. 2B shows a physical, three-dimensional embodiment of an automated health monitoring station in accordance with the present invention.

FIG. 2A shows one embodiment of an automated health monitoring station 104. FIG. 2B shows a physical representation of one embodiment of an automated health monitoring station 104. The station 104 may include, but is not limited to, an image capture device 206, a height measuring device 214, a weighing device 204, a computer 210, a biometric identification system 202, or a connection 208 to a network 212.

The image capture device 206 is any device that can create a picture or image of the participant 102 before, during, or after the weighing process. Image capture devices 206 include, but are not limited to, automated camera systems, web cameras, or video cameras. In an exemplary embodiment, the image capture device 206 is a digital camera. The image capture device 206 can be mounted on a detachable arm that allows the device 206 to be moved across the room to capture a full body view of the participant 102 while the weight measurement is being made. In an exemplary embodiment, the camera 206 is on a portable mounting that has a 15 foot long cord, allowing the camera 206 to be placed in a location that permits a full body viewing angle. In another embodiment, the weighing device may be moved away from the health monitoring station and the image capture device to allow the image capture device to capture a full-length image of the participant with a frontal view. This full-length photo ensures that the participant 102 is not leaning on anything that might artificially raise or lower his weight. The device 206 can send its image to the computer 210 or over a network connection 208. Image capture devices 206 are well known in the art and will not be explained further.

A height measuring device 214 may be any device used to accurately determine the height of the participant 102. An adjustable height measuring device 214 can enable the measurement of the participant's height in conjunction with the weight measurement. In an exemplary embodiment, the height measurement device 214 is a bar or mechanical armature that measures the height of the individual 102. The measuring device 214 can contain a pressure sensitive switch (not shown) that will only perform the height measurement once the arm is lowered onto and then receives light pressure against the participant's head. The device 214 may be retractable and can be stored inside a main vertical support beam. The first time a participant 102 uses the station, the system prompts the participant 102 to extend the measuring device 214. With the device extended, the participant 102 presses the top bar toward their head until the tone sounds and the height is recorded. Another height measuring device 214 may be an optical or electronic sensors or devices. For instance, a beam of light and a light sensing diode may pass down the sides of the person until the beam of light is broken and identifies the top of the person. The device can record the height at the point the top of the person is identified by the light beam being broken. These optical and electronic devices may have problems with hair and other impediments and is not optimal.

The station 104 may also include an identification device 202 and, in many embodiments, a biometric identification device 202. While a biometric identification device 202 will be used to explain the invention hereinafter, other identification devices 202 may be used with the present invention. For instance, a participant 102 may be able to enter an identifying log-in into the station 104. This log-in may contain a unique log-in name, like "jsmith1204", and password, like "marycontrary448", that each participant 102 will have assigned to them. With this information entered into the station 104, the station 104 will be able to identify the participant 102.

A biometric recognition device 202 enables identification of the participant 102. A biometric device 202 can be any type of recognition device that enables identification of a participant 102. This device 202 is any system or means of recognizing a person through biometric data Biometric data is any biological attribute that is unique to the person. Some examples of biometric identification devices 202 may include, but are not limited to, retinal scanners, fingerprint scanners, handprint scanners, footprint scanners, facial recognition devices and cameras, DNA identification, blood typing devices, and voice recognition devices. In one embodiment, a fingerprint reader 202 is attached to an upper platform of the station 104. When the participant 102 is standing on the scale 204, the fingerprint reader 202 becomes active. In another embodiment, the weighing device may be moved away from the station and thus, may not allow the participant to use the fingerprint reader simultaneously with the weighing device. However, the station may still synchronize the picture and the weight measurement. When the participant 102 places his or her finger in the reader 202, the system 104 looks up the participant 102 in a database 218. Once the participant 102 is identified, a reading is simultaneously taken from the scale 204 and the digital camera 206. This process ensures that the weight measurement is associated with the correct participant 102.

The computer 210 is any type of electronic processor 216 or device that can function as a connection hub for all other devices, a connection to the Internet 208, a data entry device or man/machine interface 222 for new user login, a display device 220 for messages to the participant 102, memory 218 for storage of data, and processing of commands and calculations for the system. In some embodiments, the computer may also include a printing device (not shown) that can provide a paper or other "hard copy" article that includes some weigh-in information. The computer 210 can prompt the user 102 for their name and age during first use and receive this data from the person 102. During subsequent weigh-ins, a display 220 prompts the user 102 for any additional information. The computer 210 may contain a local hard drive 218 or other memory 218 to temporarily store measurement data or other data, such as fingerprint scans, images, data entered by the participant 102, or data received from the other devices. Either the computer 210 or the connected devices may place a time and date stamp on any information created during the weigh-in. The time and date stamp refers to the process of synchronizing all of the authentication and measurement steps and grouping them with a label that indicates exactly when the measurements were taken. In addition, the computer 210 may securely transmit any data over the network connection 208 and onto a network 212. The computer 210 may be a specially-made system, a laptop computer, a desktop computer, a server, a mainframe, or other similar device. Computers 210 are well known in the art and will not be explained further.

A weighing device 204 may be included with the station. In an exemplary embodiment, the weighing device 204 is automated. One embodiment of the weighing device 204 may be a digital scale that measures the participant's weight and sends the data to the computer 210. While a scale 204 is described and shown, it is also envisioned that the station 104 may be able to measure other health functions. For instance, some systems 224 may be included in the station that may measure body fat, blood pressure, blood sugar, cholesterol, or other health data. This data may be assembled in a digital format and sent to the computer 210 for processing. Thus, while a weighing device 204 is used in this description, the health monitoring station 104 is not limited to that one embodiment. A weighing device 204 can measure the weight of the participant 102. Additionally, this weighing device 204 may be capable of estimating body fat percentages if the participant 102 removes their footwear before standing on the scale 204. The scale 204 can be networked with the other components of the automated health monitoring station 104 so that it performs its measurement at the same time as the fingerprint reader 202 and the camera 206 are active. All data collected may be matched to the time stamp of the fingerprint reader 202 and the digital camera 206 to ensure that correct participant 102 is using the scale 204. Digital scales 204 and similar weighing devices are well known in the art and will not be explained further.

Another device may be a connection to a network 208. This connection 208 or communications link is a means of securely transferring the measurement data from the measuring station 104 to the data center 106 or other outside entity or system. The monitoring station 104 may connect to the central data center 106 via a high speed Internet connection or via a dial-up modem using a standard analog phone line. This communication link can be encrypted to prevent unauthorized access to the measurement data being transmitted. In other embodiments, the network 212 may be to a WAN, LAN, an intranet, an internet, wireless system, or other communications network. Networks 212 and the connections 208 to those networks are well known in the art and will not be explained further.

Method of Providing an Incentive for Weight Loss

Referring to FIG. 3, an embodiment of the method to provide incentives for weight loss or weight maintenance may include several parts. An employer 108 or organization can enroll 302 or join the program, and participants 102 (and their families, if eligible) can enroll 304 or register for the program. Enrolling 304 in the program may require the participant 102 or organization 108 to submit information to an outside entity 110 or 106. For the participant, this information may include personal data. Personal data may include, but is not limited to, eating habits, exercise habits, name, address, age, gender, education achieved, or favorite activities. This data can be used by another organization to create a personal profile for the participant 102. This profile allows the organization to tailor support information for the participant 102.

Once a participant 102 registers for the program, they can utilize the health monitoring station 104 to record automatically 306 their initial weight and height or other biological data. The participant 102 presents themselves for the weight measurement. In one embodiment, presenting themselves for the automated weight measurement refers to the process where the participant 102, by themselves, enters the measurement room, removes any shoes, steps on the scale, presses their index finger on the fingerprint reader, looks at the camera, and has their weight measurement taken. The first weight measurement is obtained 306 for the participant 102 through this weighing process. A weight measurement is a value of the participant's weight. For instance, the weight measurement may be 179 pounds. The weight measurement may be compiled in any system such as English, metric, or other system.

In an exemplary embodiment, the participant 102 can privately measure their weight using the health monitoring station 104 described above. For example, the participant 102 enters a private room. Without anyone else being present, the participant 102 can make an unsupervised weight measurement. The station has a fingerprint reader for authenticating the identity of the participant 102, a digital scale 204 for recording the weight level, a digital camera 206 for saving an image of the participant 102 being weighed for verification purposes, and a height measurement arm 214 for measuring the height of the participant 102 during the participant's measurement. Thus, the station 104 allows the entire weighing process to be automated. In other words, no human intervention is needed, beyond the participant 102 standing on the scale 204, to measure the participant's weight. A small display screen 220 and keyboard 222 lets the participant 102 view the readings and interact with the system 104 if necessary. In this embodiment, the entire measuring station 104 is connected to a network 212 to transmit the measurement data to the data center 106. Participant 102 data collected should be collected in a confidential manner (by means of using a private weighing room with no other individuals present). After collection, participant health data should be secured while being transmitted to the central data collection server 206. Once on the server 206, the data again should be secured to prevent unauthorized access.

After a period of time, the program requires the participant to be weighed again. The health station 104 may obtain this next weight measurement. The weigh-ins can be used to determine progress toward a healthy weight. In most embodiments, there will be several successive weight measurements for the participant 102. These successive measurements may be periodic and planned or more erratic and unscheduled. The next weigh-in after the first weigh-in or after a previous weigh-in can be made voluntarily or at a scheduled time. In other words, the participant 102 may use the automated health monitoring station 104 at some point after a period of time without direction or they can be required to measure their weight by an organization 106, 108, or 110 at some time. The weight measurements from the initial weigh-in, the next and all subsequent weigh-ins, may be securely uploaded 314 to the data center 106. In this embodiment, the data center 106 is a large repository of all the participants' data collected while these people 102 participate in the program.

On a periodic basis, the data in the data center 106 can be analyzed 316 to determine the performance of each participant 102. Reports may be run on the data to compare each participant's starting height and weight with the most recent weight measurement. This calculation determines what amount of, if any, weight loss level the participant 102 has achieved over a given time period. Thus, between the first and the next weight measurement, a participant should wait 310 for a period of time to elapse. Also, a period of time may elapse between each successive next measurement. In an embodiment of the program, this time period might be a three month span. However, the time period may be any duration of time. In most embodiments, the time period will be greater than a day because it is unlikely a person can lose any significant weight in a single day.

The performance data can be sent 318 to a third party administrator 110 or an employer 108. Following the receipt of the performance data, the participating organizations 106, 108, or 110 can determine 320 if the participant lost weight and deserve a monetary incentive 114. If the participant did lose or maintain their weight 322, the employers 108 may provide the monetary incentives 114 by writing 324 the appropriate checks to the employees 102 that have successfully reduced or maintained their weight level. In other embodiments, the third party administrator 110 or the data center 106 may write the checks or make the cash payments. Other forms of payment are also acceptable including, but not limited to, direct deposit, cash payment, and credit to some participant account. In other embodiments, the incentives and the form of providing those incentives may include giving gifts, like cruise giveaways, contest prizes, or other similar incentives.

Besides using simple weight measurements, a scale or some other measurement may be used to determine weight loss, including, but not limited to, a ratio between weight and height, body mass index (BMI), or a body fat measurement. BMI is determined by your weight divided by your height. Based on an individual's height, there is an appropriate healthy weight range. Measuring an individual's BMI determines where they are with respect to the target healthy weight range.

The present invention can provide an ongoing incentive for weight loss. An incentive 114 can mean any financial health care premium reward paid to the participant 102 for lowering or maintaining their weight. A health insurance premium reward 114 is the monetary incentive 114 paid back to participants 102 who participate in the program and successfully lower or maintain their weight. As long as they maintain their weight level, the participant 102 will continue to receive the premium reward. The duration of the program may vary as some organizations may pay the incentive for one year or other time period and some organizations may pay the incentive perpetually. In other embodiments, we are also using a concept where at the beginning of each year, a new baseline weight may be set. Thus, if a participant starts at 220 pounds, and loses 22 pounds in year one, they would get paid on that 10% weight loss. At the start of the second year, their new baseline weight is now 198. Their BMI target is 174, so they still have weight to lose. If they lose more weight in year 2, they can get reward checks, but will receive incentives for losing weight from the new baseline weight of 198. This embodiment will help reduce or regulate the amount of the incentives paid each year. By providing a periodic monetary incentive 114 to lower or maintain a participant's weight, the participants 102 can receive ongoing positive reinforcement for successful weight loss. In cases where the participant 102 regains 326 lost weight, they receive negative reinforcement in the form of a reduction 328 or complete elimination of their incentive. This system of positive and negative reinforcement provides a continuing incentive for weight loss.

Several different methods for determining weight loss may be used in the method 300. One method may determine progress by comparing the difference between the first weight measurement and the next or the latest weight measurement. For instance, the participant 102 may make a first weight measurement of 220 pounds. After successive periods of three months, the participant 102 repeats the weight measurement. In the example, the participant may have made five more measurements that were 222, 215, 210, 211, and 208. In one embodiment, all measurements would be compared to the first weight measurement. Thus, the second weight measurement of 222 would be compared to the first measurement of 220. A weight increase difference of 2 pounds would be determined. With one embodiment, the participant 102 may only receive a monetary incentive if the next weight measurement is below the first measurement. In the example, the participant 102 would receive no incentive 114 for an increase of 2 pounds. However, the participant 102 would receive a monetary incentive 114 because the difference between the first weight measurement and the second weight measurement is a loss of five pounds. The monetary incentive 114 may increase if the difference in weight loss increases. Thus, the monetary incentive may grow as the difference in weight loss for the third measurement is 10 pounds compared to a five pound loss for the previous measurement. Likewise, the monetary incentive may decrease if the difference decreases as when happened when the fourth measurement showed a nine pound loss, which was less than the ten pound loss for the previous measurement.

In another embodiment, the previous weight measurement is compared to the current weight measurement. Thus, the previous weight measurement may be considered the first weight measurement and the current weight measurement may be considered the next weight measurement. In this embodiment, the monetary incentive 114 may only be given if the next weight measurement is below the first weight measurement. The greater the difference between the two weight measurements, the greater the monetary incentive 114. If the weight measurements are the same, no incentive 114 may be given. Likewise, if the next weight measurement is greater than the first weight measurement, no incentive 114 may be given. If a set monetary incentive 114 was already being given, a difference between a lower first measurement of 210 pounds and a higher next measurement of 211 pounds may incur a decrease in the incentive 114.

A weight management program may employ a different methodology. For instance, the goal of the program may not be weight loss but weight maintenance. In this embodiment, the participant 102 may be given monetary incentives 114 to keep the weight the same. The term "same" may be misleading. Minor fluctuations in a person's weight are normal and expected. However, the weight management program may need to know when the weight changes are normal and when they show a significant change. Therefore, the program may establish a small deviation for within which a participant's weight may fluctuate. This small deviation may be any number of pounds or fractions of a pound. As an example, the program may allow fluctuations of two pounds above or below the weight to be maintained.

Another embodiment may establish weight loss goals. For every weight loss goal, a monetary incentive 114 of differing amount may be assigned to the goal. If the participant 102 meets or exceeds the goal, they receive the monetary incentive 114 assigned to that goal. These goals may be expressed in terms of pounds to lose or in a percentage or fraction of weight to lose. For instance, the program may establish a three weight loss goals for the example mentioned above— 215, 210, and 205 pounds. As explained, a monetary incentive 114 may be given when the participant 102 either meets or exceeds the goal. After each weigh-in, the measurement is compared to the different weight loss goals and a determination is made as to whether and which monetary incentive 114 the participant 102 is to receive for meeting or exceeding one or more weight loss goals. For example, when the participant 102 above reached 215, they would receive the monetary incentive 114 assigned to meeting the weight loss goal of 215 pounds. At the next weigh-in, the participant 102 would receive the next increased monetary incentive 114 for meeting the 210 pound weight loss goal. However, the monetary incentive 114 would be decreased at the next weigh-in because the participant's weight went above the 210 pound weight loss goal. Instead, the participant 102 would receive the incentive 114 they previously received when reaching the 215 pound goal. At the last weigh-in, the participant 102 would exceed the 210 pound goal and receive the incentive 114 for that goal. Yet, the participant 102 would still not receive the incentive for the 205 pound goal. If the participant 102 maintained their weight between two goals, they would continue to receive the same incentive 114 assigned to the previous goal that was attained. Thus, the incentives increase 114 for meeting or exceeding successive weight loss goals, decrease for failing to meet weight loss goals previously achieved, and stay the same for neither meeting or exceeding a successive weight loss goal nor neither failing to meet nor failing to exceed a previously achieved weight loss goal.

In another embodiment, the weight management program may attempt to change the participant's body composition. A person's body composition may be the amount of body fat to muscle mass or some other health condition, such as cardiovascular fitness or cholesterol level. For instance, the weight loss program may attempt to encourage a participant to lose 10 pounds of body fat, and replace it with 10 pounds of muscle mass. The participant's weight, which may have been ideal on the BMI, may be unchanged, but their overall health would be improved. Thus, the health monitoring station and the health maintenance program can track body fat or other health information.

Participants 102 can employ any of a number of effective weight loss programs. Numerous weight loss programs have demonstrated an ability to help participants 102 lose weight. The addition of the ongoing incentive 114 is the missing element needed to sustain the weight loss. In one embodiment of the invention, the weight loss program utilized will focus on being realistic for the participants 102. The goal is for the program of diet and exercise to be habit forming for all participants 102. The ideal program utilizes simple fitness activities that don't require costly equipment. Typical activities may include walking, stretching, and simple lifting of household items. The typical diet program utilized will direct participants 102 toward food ideas and eating patterns that are both healthy and satisfying, resulting in an approach that is sustainable and enjoyable.

The measurement of participants' weight level may be performed on a periodic basis, as evidenced by branches 322 and 326. In a typical embodiment of the invention, this period may be quarterly. The measurement is performed directly by the employee 102 in a private location to ensure that sensitive weight data remains private. The weight measurement station 104 can be configured to collect the participant's weight in an automated manner, utilizing procedures to ensure that the data collected is accurate. This weight measurement process may include the participant 102 presenting themselves for the measurement, verifying the identity of the person, automatically weighing the person, and transmitting the weight or other data to the data center 106. As previously explained, presenting the person for weighing may include, but is not limited to, the person arriving at the health monitoring station facility at a scheduled time, the person entering the private room or area, the person removing their shoes, or the person stepping onto the weighing device.

The measurement of the participant's weight must be performed in a manner that correctly verifies the identifying information of the participant 102 (such as name, employee number, date of the measurement, etc.) and matches it with the current weight level. This is necessary to prevent fraudulent reporting of the participant's weight. A typical embodiment of the invention will utilize technology such as electronic fingerprint readers or other biometric identification device 202 to authenticate correctly and to match correctly the participants 102 with their weight measurements.

After identification is done, the participant 102 will be weighed automatically by the weighing device 204. In one embodiment, an image may also be automatically created by an image capture device of the participant approximately when they are being weighed. Thus, the image is captured during, just before, or just after the weigh-in. This image further prevents fraud by showing who is being weighed and how they are being weighed. In some embodiments, the image may be captured, the weight may be measured, and the identity verified in temporal proximity. In other words, these activities may occur at the same time or within seconds or fractions of a second.

The invention also embodies the measurement being transmitted to the data center 106 over the network connection 208. Either at the data center 106 or at the automated health monitoring station 104, the health data of the participants 102 may be stored and manipulated. In one embodiment, the data may be used to create custom participant profiles. Custom participant 102 profiles can be any database or record of the data that may include, but is not limited to, the participant's age, gender, current fitness level, or current physical activity level. This profile can be used to create customized diet and exercise programs for each individual. The data collected can form individual participant health data files. These files may include, but are not limited to, the data collected by the automated health monitoring station 104, including: date, time, weight, height, user ID, and camera image. Aggregate participant health data is a collection of data representing multiple participants 102. This data is used to examine performance trends in the overall participant group.

An embodiment of the invention can include providing support to the participant or an automated participant support system. The automated participant 102 support system refers to the system that delivers diet, exercise, and supplement information to the participants 102. This system can provide participants 102 with daily support information based on the particular weight loss program being utilized. This support information may be delivered through numerous channels to provide the most effective communication with the participants 102. While one delivery channel may be e-mail, support information may also be delivered to pagers, cellular phones, fax machines, etc.

From the foregoing, it will be appreciated that although the weight loss incentive program described above may include more or less of the components as discussed, the described method will result in ongoing weight loss success for participants 102.

EXAMPLE

The invention provides a method and an apparatus for creating long-lasting incentive for weight loss. The following is an example of an embodiment of the invention. This represents one of many different implementation approaches that could be utilized to deploy the invention.

The incentive component of the invention is the key to creating a lasting effect on the health of participants 102. It changes a participant's plan for weight management from a temporary plan (with temporary results) to a permanent program where success at weight management is continually reinforced.

In partnership with third party administrators 110 (TPAs) and self-insured entities, a data center 106 can provide organizations (and their participants 102) with a reward on their monthly insurance premiums based on the weight of each participant 102 (using a modified BMI scale). The health insurance premium reward is calculated based on a participant 102 reducing their weight at increments along a scale that targets the Body Mass Index (BMI) target weight charts. The closer to the BMI weight target a participant 102 comes, the larger the reward. For instance, for every ten pounds that a person loses, the premium for that person will be reduced by $100 a year. In another embodiment, the incentive 114 is paid as long as progress is made at each weigh-in. In other words, at every weigh-in the participant 102 has reduced their weight from the last weigh-in. If the progress ceases or the participant's weight increases, the payments may be lowered or cancelled. If the participant 102 reaches their ideal weight, the payment may not increase but reach a maximum payment.

The company or organization pays the full premium (age-based) each quarter to the insurance company or third-party administrator. At the end of each quarter, the participants 102 perform a weigh-in to determine their discount for the upcoming quarter. At the end of the following quarter, they receive a check for their discount due to being at a lower weight for the previous quarter. Participants 102 who reduce their weight will continue to receive the reward 114 as long as they near or maintain their target weight and the insurance remains in force. This constant and consistent monetary payment provides the ongoing incentive 114 for participants 102 to maintain a healthy lifestyle.

If the participant 102 remains at their previous qualifying weight level for a new quarter, they will continue to receive the same reward 114. If the participant 102 gains weight and moves out of the fitness stage they are currently in, their reward 114 will be reduced to the proper level based on their weight. If they move back to their original weight, the rewards 114 will no longer be paid. If the participant 102 loses additional weight and moves to a new fitness stage, they will receive the appropriate increased reward 114.

The weight loss targets of the invention can be based on the Body Mass Index (BMI) scale. While the BMI targets provide the ultimate weight goal of the program, they are too aggressive to attain in one large step. In order to create a manageable path to success, the weight management program can establish interim steps that gradually take an individual 102 from their current weight to the ideal BMI weight. In keeping with the theme of being realistic, the two components to the Weight Management Program are based on easy to achieve benchmarks that can be integrated into an individual's daily routine on a sustainable basis.

An embodiment of a BMI scale that may be used is as follows:

Stage 1: 5% body weight reduction
Stage 2: 10% body weight reduction
Stage 3: Reaching the BMI target range for a given height Based on the experience of each insurer, organization, or employer these stages can be used to determine the amount of premium reward received by each participant 102.

To assist the participant 102 lose weight the weight management program may focus on diet and exercise. In one embodiment, the elimination and moderation of sugars, carbohydrates, and alcohol, combined with consistently decreasing portions over an extended period will bring about the desired weight loss. However, a realistic way of eating must be incorporated with a regular exercise program. A restrictive diet required to take off years of fat build up, provides so little food that the dieter can't continue for a long period of time. Therefore, in creating a new habit of eating, attention must be given to the reality of our everyday living. Creating a set of stringent, never to be broken rules is doomed to failure. However, the "habit changing" methodology requires enough structure to encourage "weight control" over the long-term.

The eating program can be based on six smaller portioned meals per day: breakfast, mid-morning snack, lunch, mid-afternoon snack, dinner, and after dinner snack. This often means eating a meal when one isn't hungry. This diet is in contrast to the typical two meals eaten in the United States (lunch and dinner.) The content of the diet revolves around avoiding certain food items such as sugars, alcohol, high-carbohydrate processed foods, and fatty foods with little nutritional content. The target foods are those with moderate carbohydrates, high-protein, moderate fats, and high in vitamins and nutrients. Additionally, there is a free day each week during which the individual may eat whatever they would like.

The exercise program may be based on a simple, realistic approach tailored to the capabilities of the participant 102. Beginning participants 102 who have not engaged in physical activity for some time will begin by simply walking and performing stretching exercises. Advanced participants 102 will utilize running and biking for cardiovascular exercise and resistance training for muscle development. The ultimate goal is to develop a healthy level of cardiovascular fitness, where the participant is able to walk or perform cardio exercises for 1 hour per session, 3 times per week. Additionally, for strength training the goal is to develop beneficial muscular strength to promote good health and increase the level of fat burning. Successful participants will be able to successfully perform strength related exercise using items such as exercise resistance bands, free weights, or weight machines.

When a participant 102 enrolls in the weight management program, they may fill out a profile form that captures key information about the participant 102. Some of the information collected may include, but is not limited to: name; date of birth; weight; current level of physical ability; desired fitness level; desired diet program; desired length of time to complete weight loss stage of the program; types of exercise preferred; preferred time of day for workouts; or type of foods preferred. Based on this information, the system can create a custom program of information on diet and exercise. To assist the participants 102 in successfully changing their eating and exercise habits, the invention utilizes a daily communication to each participant 102. This newsletter may be delivered early in the morning, for instance 3:00 a.m., to allow the participant 102 to view the information for the coming day and take action. The participant 102 can determine which communication method to use to receive daily updates. The default delivery method may be email. Some delivery methods include, but are not limited to: email; pager; customized web portal; print, or printing web site pages.

The weight management program requires a participant 102 to periodically measure and report their weight. To make the program run efficiently and effectively, this process can be done in an automated fashion that reduces human labor costs, eliminates fraud, and ensures participant 102 privacy. The solution is an automated health monitoring station 104 that securely transmits health information to the insurance companies in order to calculate and process reward incentives 114. On a quarterly basis, participants can proceed to the automated health monitoring station 104 and record their weight. This data is sent to the servers and used to determine reward check calculations.

To insure privacy, the participant 102 may weigh themselves without a technician present. The participant 102 can take the measurement in a private room with no other individuals present because the measurement station is automated. At the end of the measurement session, the readings are cleared from the device and all displays are reset for the next participant 102. After each participant 102 uses the health monitoring station 104, the data is sent securely (in one embodiment using SSL) via the Internet to the centralized server 106. This prevents any data from being intercepted or viewed as it is sent to the server 106. Once that data arrives, it is stored in a secure database that is protected by numerous data protections mechanisms (such as firewalls, encryption, physical security, etc.) to ensure that it is not accessible by unauthorized parties. This security process is similar to the level of protection applied to financial data stored at a bank's data center 106.

To eliminate fraud in the program, the automated health monitoring station 104 may provide accurate identification of the participant 102 being measured. This identification is necessary to avoid any abuse of the system by having one participant 102 perform a weight measurement in the place of another or other type of fraudulent practices. To address this issue, the health monitoring station 104 can use a biometric identification device 202. In an exemplary embodiment, this device 104 may be a simple electronic fingerprint reader. This identification approach also allows the identification process to be automated and performed in a manner that ensures participant privacy. The identification of participants 102 can be achieved by having the participant 102 step on the scale and press their finger on the fingerprint reader. This eliminates the need for any other human resources to be involved in the identification process. Using an electronic fingerprint reader can provide a failsafe method for determining which participant 102 is currently using the system. This biometric identification 202 eliminates the issues and limitations involved with using a traditional user ID and password approach. Due to the automated nature of the fingerprint system, the participant 102 can use the device in private with no other individuals present. This privacy regiment helps ensure that participant health information is collected in a confidential environment.

To weigh-in a participant 102, a monitoring station 104 can be located in a private room where the participant 102 can privately measure his or her weight. When a participant 102 enters the monitoring area, they remove their shoes and step onto the scale. Next, they look at the camera and place their finger on the fingerprint reader 202. The fingerprint reader 202 confirms the identity of the participant 102 and then records the time, date, body weight, photograph and user ID of the participant 102. This information is then sent in real time to the central participant health database 106 via the Internet 212.

After each participant 102 uses the health monitoring station 104, the data can be sent securely (using SSL) via the Internet 212 to the centralized server 106. Alternatively, the participant 102 data can be stored locally and then sent in a batch mode (hourly, weekly, monthly, etc.) to the data repository. The data stored for each participant 102 weigh-in may include: weight; height ($1^{st}$ weigh-in only); picture; date; positive ID via fingerprint; name; ID number; etc.

An employer 108 health plan administer gateway 116 can allow the administrator at the employer's 108 office to log in and view current health payments and discounts for participants 102. The health plan administrator may access the following information including, but not limited to: a list of participants 102; discounts paid by participant 102; or total number of pounds lost. This application can be accessed over a secure (SSL) encrypted channel to ensure that no unauthorized access is permitted. An insurance company gateway 112 can provide access to the insurance company 110 that is sponsoring the invention. The application allows authorized personnel at the insurance company 110 to monitor the performance of a participating corporate customer (i.e. the employer 108). Information available in the insurance company gateway 112 includes, but is not limited to: company name; company address; company locations; participants' names, ages, weights stored for each weigh-in with time & date stamp, pounds lost; or a history of rewards earned. This system can also allow the insurance company 110 to issue a quarterly "scorecard" that reports, at a high level, on the performance of the participants 102. The system may also automate the generation of checks for each participant 102 due a reward.

An additional component of the incentive program may include support systems 118. Changing of human behavior is extremely difficult, and without a peer support group, it is nearly impossible. Because the invention serves the Corporate-Group Health Insurance market, a peer support group is automatically in place. Many of the participants 102 see each other on a daily basis. When several have taken the challenge of meeting the BMI required weight, and are working toward receiving a monthly check, the group will provide support 118 for their individual efforts. As individuals successfully reduce their weight, other participants are motivated to replicate their success. New participants 102 want to join the program and existing ones want to continue participating. In another embodiment, a method is disclosed that offers reinforcement daily thru educational, motivational, and encouraging emails and constant reminders of the benefits of losing weight.

In another embodiment, to create targeted support information 118 for each participant 102, a method is provided that collects a detailed profile on each participant 102. This information 118 may be confidential and may only be used to provide specialized information to the participant 102 for their customized eating, exercise, and supplement programs. In a further embodiment, the invention comprises a system 118 for providing educational and motivational information to participating participants. This information 118 covers eating, exercise, and supplements. By receiving this information 118 on a regular basis, the participant 102 is equipped with the necessary information required to make changes to their health. Included with this information 118 is motivational information, quotes, and before and after success stories with photos that also serve to encourage the participant 102 to stay with the program.

Several of the entities in the system may access the health data. However, to protect participant 102 privacy, the employer 108 may not have access to individual health records of its participants 102. It only receives aggregate information and quarterly check information. The sponsoring insurance agency, employer, or organization (depending on who is managing the program) can access the detailed participant 102 information for the purposes of calculating earned rewards. Participants 102 can have access to their own records to verify that the information is correct. This access can be conducted via a secure Internet connection.

We claim:

1. An automated health monitoring station to obtain health data of a person, comprising:
   a. a computer operatively coupled to a connection configured to receive data from and communicate data to a data center over a network;
   b. an automated weighing device communicatively coupled to the computer, the weighing device configured to communicate with the computer, the automated weighing device adapted to receive the person's feet as the person steps on the automated weighing device; and
   c. an image capture device communicatively coupled to the computer, the image capture device positioned with respect to the automated weighing device to obtain an image of a full length of the person, the image capture device configured to capture said image of the person while the person is on the automated weighing device.

2. The automated health monitoring station according to claim 1, wherein the automated weighing device is a digital scale.

3. The automated health monitoring station according to claim 1, wherein the image of the person obtained by image capture device is used by the computer to identify the person.

4. The automated health monitoring station according to claim 1, further comprising a height measuring device.

5. The automated health monitoring station according to claim 4, wherein the height measuring device is a mechanical armature that lowers onto a person's head.

6. The automated health monitoring station according to claim 4, wherein the height measuring device is an optical device that identifies a top of a person and determines a height of the person using the identification.

7. The automated health monitoring station according to claim 4, wherein the height measuring device is an electronic device that identifies a top of a person and determines a height of the person using the identification.

8. The automated health monitoring station according to claim 1, wherein the image capture device is one of an automated camera system, a web camera, a digital camera, or a video camera.

9. The automated health monitoring station according to claim 1, wherein the network is one of a WAN, a LAN, an intranet, an internet, or a wireless system.

10. The automated health monitoring station according to claim 1, wherein the computer includes one or more of a man machine interface, a processor, a memory, a printing device, or a display device.

11. The automated health monitoring station according to claim 1, wherein the computer receives data from the person.

12. The automated health monitoring station according to claim 11, wherein the computer stores data from the person and the automated weighing device.

13. A method for automatically weighing a person, comprising:
   a. providing an automated health monitoring station to the person, the automated health monitoring station comprising a computer operatively coupled to a connection, the connection configured to communicate with a data center over a network and one or more devices; an automated weighing device communicatively coupled to the computer, the weighing device enabled to communicate with the computer, the weighing device adapted to receive the person's feet; and an image capture device communicatively coupled to the computer and positioned relative to the weighing device to capture an image including a view of a full length of the person while the person is standing on the weighing device to confirm an accurate weight;
   b. presenting the person for weighing;
   c. verifying the identity of the person;
   d. automatically weighing the person;
   e. during the weighing operation, capturing the image of the full length of the person;
   and
   f. transmitting a weight and the image to a data center.

14. The method according to claim 13, wherein presenting the person includes one of the person entering a room or area, the person removing their shoes, the person arriving at a scheduled time, or the person stepping onto the automated weighing device.

15. The method according to claim 13, wherein verifying the identity of the person further comprises verifying with a biometric identification device.

16. The method according to claim 15, wherein the biometric identification device is one of a fingerprint scanner, a retinal scanner, a blood typing device, a DNA identification device, a handprint scanner, a footprint scanner or a login password.

17. The method according to claim 13, wherein verifying the identity of the person is done by the person entering an identifying log-in into the computer.

18. The method according to claim 17, wherein the identifying log-in includes a unique log-in name and a unique password.

19. The method according to claim 13, wherein automatically weighing a person comprises using a digital scale.

20. The method according to claim 13, further comprising automatically measuring a height of the person.

21. The method according to claim 20, wherein the height of the person is measured with a height measuring device.

22. The method according to claim 21, wherein the height measuring device is a mechanical armature that lowers onto a person's head.

23. The method according to claim 21, wherein the height measuring device is an optical device that identifies a top of a person and determines a height of the person using the identification.

24. The method according to claim 21, wherein the height measuring device is an electronic device that identifies a top of a person and determines a height of the person using the identification.

25. The method according to claim 13, wherein the image capture device is one of an automated camera system, a web camera, a digital camera, or a video camera.

26. The method according to claim 13, wherein transmitting the data occurs over a connection to a network.

27. The method according to claim 26, wherein the network is one of a WAN, a LAN, an intranet, an internet, or a wireless system.

28. The method according to claim 13, further comprising storing the data on the computer.

29. The method according to claim 13, wherein the computer includes one or more of a man machine interface, a processor, a storage device, a printing device, or a display device.

30. The method according to claim 28, wherein the computer receives data from the weighing device and the image capture device.

31. The method according to claim 13, wherein the computer transmits the data to the data center.

32. The method according to claim 13, wherein the computer receives data from the person.

33. The method according to claim 13, wherein automatically weighing the person and verifying the identity of the person occurs in temporal proximity.

34. An apparatus for obtaining health related data, the apparatus comprising:
   a computer comprising a connection device, the connection device enabled to transmit data to and receive data from a database and one or more devices;
   a weighing device operatively coupled to the computer, the weighing device enabled to calculate a weight of a user and communicate with the computer; and
   an image capture device operatively coupled to the computer and the weighing device, the image capture device positioned relative to the weighing device to capture a substantially full length image of a user, the image capture device configured to capture said image while the user is being weighed by the weighing device, the image capture device enabled to communicate with the computer.

35. The apparatus according to claim 34, wherein the image capture device is a camera.

36. The apparatus according to claim 34, wherein the weighing device is a digital scale.

37. The apparatus according to claim 34, further comprising a biometric device to confirm an identity of the user.

38. The apparatus according to claim 37, wherein the biometric device comprises one or more of a fingerprint scanner, a retinal scanner, a blood typing device, a DNA identification device, a handprint scanner, a footprint scanner, voice recognition device or a facial recognition device.

39. The apparatus according to claim 34, wherein the network is one of a WAN, a LAN, an intranet, an internet, or a wireless system.

* * * * *